(12) United States Patent
Satoh et al.

(10) Patent No.: US 7,939,340 B2
(45) Date of Patent: *May 10, 2011

(54) HYDROXYL RADICAL DETECTION

(75) Inventors: Andrea Yuki Satoh, Holt, MI (US);
Susan J. Masten, Ancaseter (CA);
James Trosko, Okemos, MI (US)

(73) Assignee: Board Of Trustees Of Michigan State University, East Lansing, MI (US)

(*) Notice: Subject to any disclaimer, the term of this patent is extended or adjusted under 35 U.S.C. 154(b) by 813 days.

This patent is subject to a terminal disclaimer.

(21) Appl. No.: 11/478,959

(22) Filed: Jun. 28, 2006

(65) Prior Publication Data

US 2008/0003687 A1   Jan. 3, 2008

(51) Int. Cl.
*G01N 21/77* (2006.01)

(52) U.S. Cl. ........ 436/169; 436/131; 436/164; 436/514; 436/518; 435/7.1; 435/7.4; 435/17; 422/56; 422/57; 422/82.05; 422/61

(58) Field of Classification Search .................... 422/55, 422/56, 58, 57, 186, 82.05; 436/131, 164, 436/169, 514, 518, 536; 435/7.1, 7.4, 7.94, 17

See application file for complete search history.

(56) References Cited

U.S. PATENT DOCUMENTS 5,726,565 A * 3/1998 Uchiyama et al. ............... 324/94
6,790,411 B1 * 9/2004 Read .............................. 422/28

OTHER PUBLICATIONS

Buettner et al, 1984, Springer-Verlag, 23: 235-243.*

* cited by examiner

*Primary Examiner* — Jill Warden
*Assistant Examiner* — Sally A Sakelaris
(74) *Attorney, Agent, or Firm* — Medlen & Carroll, LLP

(57) ABSTRACT

The invention relates to compositions, kits and methods used in hydroxyl radical detection. In some embodiments, the invention relates to compositions comprising a dye preferably methylene blue immobilized on a substrate. In additional embodiments, the invention relates methods of correlating color changes of a dye to the presence or absence of hydroxyl radicals. In some embodiments, the invention relates to a methylene blue dye containing test strip and its use in a method for detecting the presence of hydroxyl radicals.

9 Claims, 8 Drawing Sheets
(2 of 8 Drawing Sheet(s) Filed in Color)

Hydrophobic Barrier (thick black line)

PLATE #1 EXPT. #6 8/31/04
Methanol (MeOH)/Chloroform 2:10
2 µL        3 µL Fenton
9 mM       Sample
BA/MeOH   @ 30 min

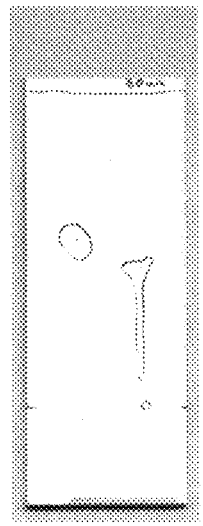

FIG. 2A

PLATE #2 EXPT. #6 8/31/04
Methanol/Chloroform 2:10
1 µL        3 µL Fenton
9 mM       Sample
HBA/MeOH  @ 30 min

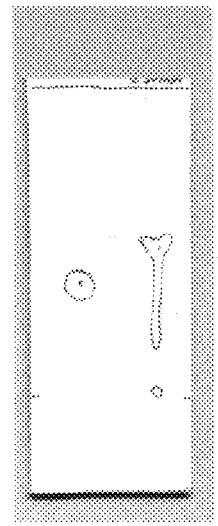

FIG. 2B

PLATE #3 EXPT. #6 8/31/04
Methanol/Chloroform 2:10
2 µL        3 µL Fenton
Mixed      Sample
Standard   @ 30 min

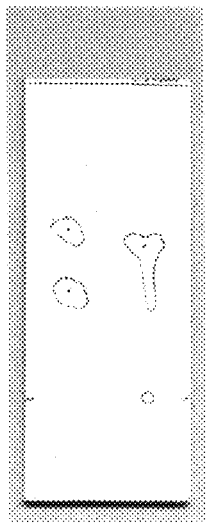

FIG. 2C

PLATE #4 EXPT. #6 8/31/04
Methanol/Chloroform 2:10
2 µL        3 µL Fenton
Mixed      Sample
Standard   @ 1 hr

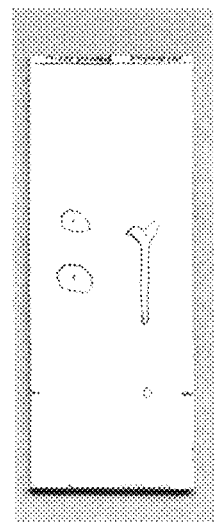

FIG. 2D

PLATE #5 EXPT. #6 8/31/04
Methanol/Chloroform 2:10
2 µL        3 µL Fenton
Mixed      Sample
Standard   @ 1 hr 30 min

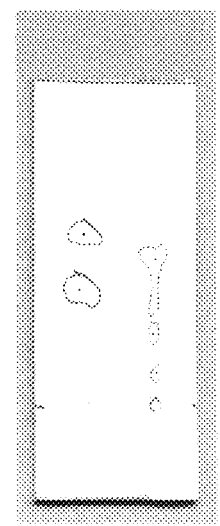

FIG. 2E

PLATE #6 EXPT. #6 8/31/04
Methanol/Chloroform 2:10
2 µL        3 µL Fenton
Mixed      Sample
Standard   @ 2 hr

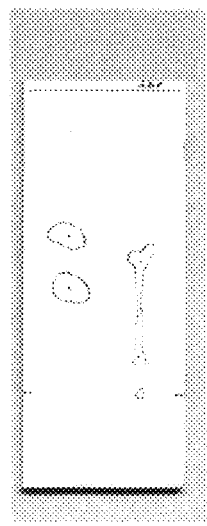

FIG. 2F

HYDROXYL RADICAL DETECTION

FIELD OF INVENTION

The invention relates to compositions, kits and methods used in hydroxyl radical detection. In some embodiments, the invention relates to compositions comprising a dye preferably methylene blue immobilized on a substrate. In additional embodiments, the invention relates methods of correlating color changes of a dye to the presence or absence of hydroxyl radicals. In some embodiments, the invention relates to a methylene blue dye containing test strip and its use in a method for detecting the presence of hydroxyl radicals.

BACKGROUND

Fenton's reagent, i.e., hydrogen peroxide, sulfuric acid, and iron $2^+$ cation, produces a solution of hydroxyl radicals. This solution is a strong oxidizer and is commonly used in environmental cleanups to decompose toxins and contaminants. Although in iron/hydrogen peroxide systems some have measured the loss of hydrogen peroxide as an indicator for hydroxyl radical formation, this approach is not entirely satisfactory because not all of the peroxide degraded is necessarily converted to hydroxyl radicals, and the complexity of the reaction often leads to the formation of a variety of species. Thus, it is desirable to identify a method for the qualitative determination of the presence of hydroxyl radicals in complex reaction systems.

Previous methods developed for the qualitative detection of hydroxyl radicals have often depended on the addition of chemical probes, such as salicylic acid, and correlating the resulting hydroxylated reaction products as an indirect measurement of the presence and level of hydroxyl radicals. In the presence of other hydroxyl radical scavenging and reacting chemicals, the addition of a chemical probe to the reaction mixture results in competition for the hydroxyl radicals and the possibility of interacting byproduct reactions. In addition, the possibility of multiple hydroxylated products often makes the detection of hydroxyl radicals complicated. Electron spin resonance can be used to detect hydroxyl radicals by measuring the electron paramagnetic spectrum of a spin adduct hydroxyl radical derivative after spin trapping. However, this requires expensive instrumentation and is not easy to carry out because of instability of hydroxyl radical spin adducts. Thus, there is a need to identify an improved method of detecting hydroxyl radicals that is easier to implement.

SUMMARY OF INVENTION

The invention relates to compositions, kits and methods used in hydroxyl radical detection. In some embodiments, the invention relates to compositions comprising a dye preferably methylene blue immobilized on a substrate. In additional embodiments, the invention relates methods of correlating color changes of a dye to the presence or absence of hydroxyl radicals. In some embodiments, the invention relates to a methylene blue dye containing test strip and its use in a method for detecting the presence of hydroxyl radicals.

In some embodiments, the invention relates to a method of determining the presence of hydroxyl radicals in a sample comprising: i) providing: a) a liquid sample and b) a bisaminophenothiazine dye immobilized on a substrate, said substrate having a color; and ii) contacting said bisaminophenothiazine dye with said sample under conditions such that said color of said substrate changes, thereby indicating the presence of hydroxyl radicals in said sample. In further embodiments, said bisaminophenothiazine dye is the compound 3,7-bis(dimethylamino)phenothiazine-5-ium chloride. In further embodiments, said bisaminophenothiazine dye, prior to step (ii), is dried on said substrate. In further embodiments, said substrate comprises one or more hydrophobic barriers. In further embodiments, said sample contains hydrogen peroxide.

In some embodiments, the invention relates to a method of determining the presence of hydroxyl radicals in a sample comprising: i) providing: a) a liquid sample and b) a dye stable to a solution of hydrogen peroxide immobilized on a substrate, said substrate having a color; and ii) contacting said dye with said sample under conditions such that said color of said substrate changes, thereby indicating the presence of hydroxyl radicals in said sample. In further embodiments, said dye is a bisaminophenothiazine dye. In further embodiments, said bisaminophenothiazine dye, prior to step (ii), is dried on said substrate. In further embodiments, said substrate is paper. In further embodiments, said substrate comprises one or more hydrophobic barriers. In further embodiments, said sample contains hydrogen peroxide.

In some embodiments, the invention relates to a method of verifying hydroxyl radical quenching in a solution comprising: a) providing, i) a solution containing a hydroxyl radical and hydrogen peroxide; ii) a quenching reagent of hydroxyl radicals; and iii) a substrate comprising a dye; b) mixing said quenching reagent and said solution containing said hydroxyl radical under conditions such that a mixed solution is formed; c) separating a sample of said mixed solution; d) contacting said sample with said substrate comprising a dye; and e) correlating said color of said dye to the existence of hydroxyl radicals in said mixed solution. In further embodiments, steps b), c), d), and e) are each done more than once. In further embodiments, said dye is a bisaminophenothiazine dye. In further embodiments, said bisaminophenothiazine dye is the compound 3,7-bis(dimethylamino)phenothiazine-5-ium chloride. In further embodiments, said hydroxyl radical quenching reagent is $Na_2SO_3$. In further embodiments, correlating said color is visually observing substantial discoloration of said test area as an indication of the presence of hydroxyl radicals. In further embodiments, correlating said color is visually observing substantially no discoloration of said test area as an indication of the absence of hydroxyl radicals.

In some embodiments, the invention relates to a substrate comprising a bisaminophenothiazine dye and one or more hydrophobic barriers. In additional embodiments, the invention relates to a kit comprising a substrate immobilized with a bisaminophenothiazine dye and a liquid transferring mechanism. In further embodiments, said liquid transferring mechanism is selected from an eyedropper or a capillary tube.

In some embodiments, the invention relates to a substrate comprising an immobilized bisaminophenothiazine dye. In further embodiments, the invention relates to a substrate comprising a test area having a bisaminophenothiazine dye enclosed by a hydrophobic barrier. In further embodiments, said hydrophobic barrier comprises an alkylalcohol and a ketone. In further embodiments, said substrate comprises one or more hydrophobic barriers. In further embodiments, said substrate comprises a test area comprising a dye having a color stable to a solution of hydrogen peroxide. In further embodiments, the invention relates to a test strip comprising a testing region defined by hydrophobic barrier, said region comprising a bisaminophenothiazine dye.

In some embodiments, the invention relates to a kit comprising a substrate immobilized with a bisaminophenothiazine dye. In further embodiments, said substrate is contained within a darkened space. In further embodiments said darkened space is the interior of a nontransparent bag.

In some embodiments, the invention relates to a method of determining the existence of hydroxyl radicals in a sample comprising: i) providing: a) a sample of a solution suspected of containing hydroxyl radicals and b) a bisaminophenothiazine dye composition; ii) mixing said sample and said bisaminophenothiazine dye composition under conditions such that a sample mixture results; and iii) correlating said color of said sample mixture with the presence or absence of hydroxyl radicals. In further embodiments, said bisaminophenothiazine dye is the compound 3,7-bis(dimethylamino)phenothiazine-5-ium chloride. In further embodiments, said bisaminophenothiazine dye composition is a solid. In a preferred embodiment, said bisaminophenothiazine dye is immobilized on a test strip. In further embodiments, said bisaminophenothiazine dye composition is an aqueous solution. In further embodiments, said sample suspected of containing hydroxyl radicals contains hydrogen peroxide. In some embodiments, correlating is visually observing discoloration of said test area as an indication of the presence of hydroxyl radicals. In some embodiments, correlating is visually observing no discoloration of said test area as an indication of the absence of hydroxyl radicals.

In some embodiments, the invention relates to a method of determining the existence of hydroxyl radicals in a sample comprising: i) providing: a) a substrate comprising a test area comprising a dye having a color stable to a solution of hydrogen peroxide and b) a sample suspected of containing hydroxyl radicals; ii) applying said sample to said test area; and iii) correlating the color of said test area with the existence of hydroxyl radicals. In a preferred embodiment, said sample is a liquid sample. In one embodiment, said sample is an aerosolized sample.

In additional embodiments, the invention relates to a method of determining the existence of hydroxyl radicals in a sample comprising: i) providing: a) a substrate containing a dye having a color stable to a solution of hydrogen peroxide and b) a solution suspected of containing hydroxyl radicals; ii) contacting said substrate with said solution; and iii) correlating the color of said test area with the existence of hydroxyl radicals. In further embodiments, said dye is a bisaminophenothiazine dye. In further embodiments, said bisaminophenothiazine dye is the compound 3,7-bis(dimethylamino)phenothiazine-5-ium chloride. In further embodiments, said substrate is paper. In further embodiments, said substrate is a glass slide coated with silica. In further embodiments, said solution contains hydrogen peroxide.

In some embodiments, the invention relates to a method of verifying hydroxyl radical quenching in a solution comprising: a) providing, i) a solution containing a hydroxyl radical and hydrogen peroxide; ii) a quenching reagent of hydroxyl radicals; and iii) a composition comprising a dye separate from said solution containing hydroxyl radical and hydrogen peroxide; b) mixing said quenching reagent and said solution containing said hydroxyl radical under conditions such that a mixed solution is formed; c) separating a sample of said mixed solution; d) contacting said sample with said composition comprising a dye; and e) correlating said color of said dye to the existence of hydroxyl radicals in said mixed solution. In further embodiments, steps b), c), d), and e) are each done more than once. In further embodiments, said dye is a bisaminophenothiazine dye. In further embodiments, said bisaminophenothiazine dye is the compound 3,7-bis(dimethylamino)phenothiazine-5-ium chloride. In further embodiments, said solution containing hydroxyl radicals contains hydrogen peroxide. In further embodiments, said hydroxyl radical quenching reagent is $Na_2SO_3$. In further embodiments, correlating said color is visually observing substantial discoloration of said test area as an indication of the presence of hydroxyl radicals. In further embodiments, correlating said color is visually observing substantially no discoloration of said test area as an indication of the absence of hydroxyl radicals.

In some embodiments, the invention relates to a method of determining the existence of hydroxyl radicals in a sample comprising: i) providing: a) a sample thought to contain hydroxyl radicals and b) a bisaminophenothiazine dye composition, separate from said sample thought to contain hydroxyl radicals; ii) mixing said sample thought to contain hydroxyl radicals and said bisaminophenothiazine dye composition under conditions such that a sample mixture results; and iii) correlating said color of said sample mixture to the existence of hydroxyl radicals in said sample thought to contain hydroxyl radicals. In further embodiments, said bisaminophenothiazine dye is the compound 3,7-bis(dimethylamino)phenothiazine-5-ium chloride. In further embodiments, said bisaminophenothiazine dye composition is a solid. In further embodiments, said bisaminophenothiazine dye composition is an aqueous solution. In further embodiments, said sample thought to contain hydroxyl radicals was obtained from an aqueous solution that had previously contained hydrogen peroxide. In further embodiments, correlating is visually observing discoloration of said test area as an indication of the presence of hydroxyl radicals. In further embodiments, correlating is visually observing no discoloration of said test area as an indication of the absence of hydroxyl radicals.

In additional embodiments, the invention relates to a method of determining the existence of hydroxyl radicals in a sample comprising: i) providing: a) a substrate comprising a test area comprising a dye and b) a sample thought to contain hydroxyl radicals; ii) applying said sample to said test area; and iii) correlating the existence of hydroxyl radicals in said sample to the extent of bleaching of said dye. In further embodiments, said dye is a bisaminophenothiazine dye. In further embodiments, said bisaminophenothiazine dye is the compound 3,7-bis(dimethylamino)phenothiazine-5-ium chloride. In further embodiments said substrate is paper. In further embodiments, said dye is substantially stable to a 3% aqueous solution of hydrogen peroxide. In further embodiments, said sample was obtained from an aqueous solution that had previously contained hydrogen peroxide.

In some embodiments, the invention relates to a method of verifying hydroxyl radical quenching in a solution comprising: a) providing, i) a solution containing a hydroxyl radical; ii) a hydroxyl radical quenching reagent; and iii) a composition comprising a dye separate from said solution containing hydroxyl radicals; b) mixing said quenching reagent and said solution containing said hydroxyl radical under conditions such that a mixed solution is formed; c) separating a sample of said mixed solution; d) contacting said sample with said composition comprising a dye; and e) correlating said color of said dye to the existence of hydroxyl radicals in said mixed solution. In further embodiments steps b), c), d), and e) are each done more than once. In further embodiments, said dye is a bisaminophenothiazine dye. In further embodiments, said bisaminophenothiazine dye is the compound 3,7-bis(dimethylamino)phenothiazine-5-ium chloride. In further embodiments, said solution containing hydroxyl radicals was obtained from an aqueous solution that had previously contained hydrogen peroxide. In further embodiments, said hydroxyl radical quenching reagent is $Na_2SO_3$. In further embodiments, correlating is visually observing discoloration of said test area as an indication of the presence of hydroxyl radicals. In further embodiments, correlating is visually observing no discoloration of said test area as an indication of the absence of hydroxyl radicals.

In some embodiments, the invention relates to a method of making a substrate comprising a dye comprising: providing a substrate and a dye; mixing said substrate and said dye under conditions that the substrate contains said dye. In further embodiments, said substrate is paper. In further embodiments, said substrate is a glass slide. In further embodiments, said substrate is a resin. In further embodiments, said dye is a bisaminophenothiazine dye. In further embodiments, said dye is 3,7-bis(dimethylamino)phenothiazine-5-ium chloride. In further embodiments said dye is N-methyl-N-[7-(methylamino)-3H-phenothiazin-3-ylidene]methanaminium chloride.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Thin layer chromatography results from using benzoic acid in an unquenched Fenton's reaction mixture. The left side of each TLC plate was spotted with samples of standards. FIGS. 2, A and B, were spotted with the standards 9 mM benzoic acid (BA) in methanol (MeOH) and 9 mM 4-hydroxybenzoic acid (HBA) in methanol, respectively. The remainder of the TLC plates (FIGS. 2, C-F) were spotted with 2 µL of a mixed standard consisting of 50 µL 9 mM BA/MeOH and 25 µL 9 mM HBA/MeOH. The right side of each TLC plate was spotted with a 3 µL sample of Fenton's reaction mixture from a particular reaction time. For FIGS. 2, A to C, the Fenton's sample was from 30 minutes of reaction, while for FIGS. 2, D, E, and F, the sampling times were 60, 90, and 120 minutes, respectively.

DETAILED DESCRIPTION OF INVENTION

Figure 1A:
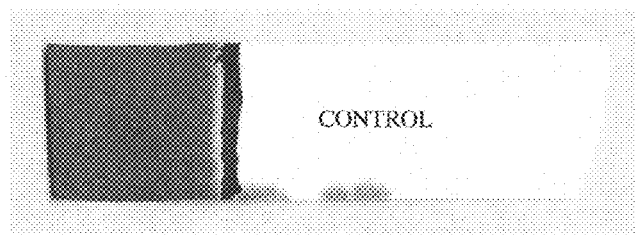
FIG. 1. Methylene blue dye test results for Fenton's reaction in ultra-pure (Milli-Q) water. For test strips (A) control (no sample added) and (B) 40 µL of Milli-Q water, no bleaching or discoloration of the methylene blue dye is observed. Test strips with 40 µL of unquenched Fenton's reaction mixture at (C) 15 minutes and (D) 30 minutes of reaction indicate the presence of hydroxyl radicals by bleaching of the methylene blue dye from dark blue to an almost white color with a dark blue outline. Test strips with 40 µL of Fenton's reaction mixture quenched with (E) 30 drops and (F) 35 drops of 10% $Na_2SO_3$ indicate the incomplete quenching and absence of hydroxyl radicals by very slight bleaching and no bleaching, respectively. The exemplary hydrophobic barrier was made using a black, fine point, permanent marker (arrow).
Figure 1B:
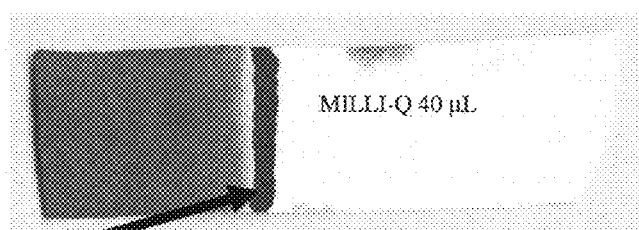
Figure 1C:
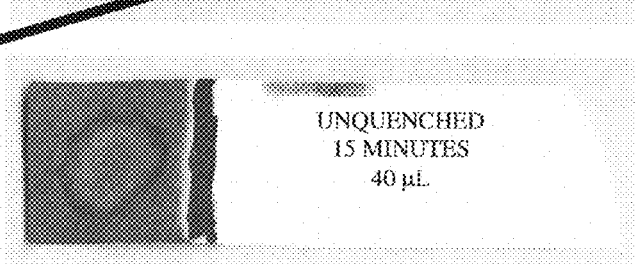
Figure 1D:
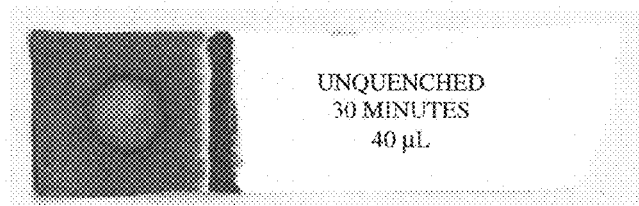
Figure 1E:
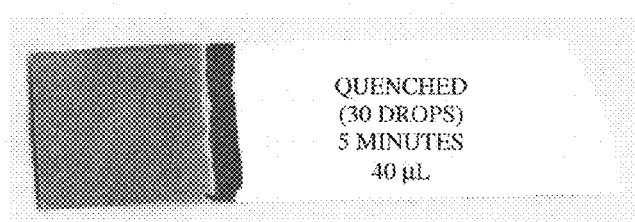
Figure 1F:
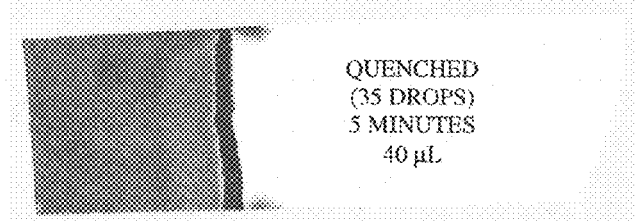

The invention relates to compositions, kits and methods used in hydroxyl radical detection. In some embodiments, the invention relates to compositions comprising a dye preferably methylene blue immobilized on a substrate. In additional embodiments, the invention relates methods of correlating color changes of a dye to the presence or absence of hydroxyl radicals. In some embodiments, the invention relates to a methylene blue dye containing test strip and its use in a method for detecting the presence of hydroxyl radicals.

A hydroxyl radical means the neutral form of the hydroxide ion having an unpaired electron, i.e., —OH.

A bisaminophenothiazine dye means the alkyl substituted or unsubstituted compound with a visual color preferably blue having the following structure:

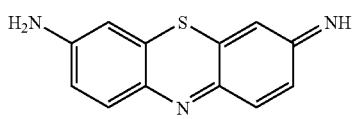

and salts thereof. The term "alkyl substituted", as used herein, means one or more hydrogen atom of the molecular arrangement is replaced with one or more alkyl group(s) or nitrogen is bound to one or more alkyl group(s) providing a nitrogen cation. The term "unsubstituted", as used herein, refers to the compound shown in the figure above.

Bisaminophenothiazine dye "salts" refers to cations and anions that make up the composition which specifically include, but are not limited to, bisaminophenothiazine dye salts having the partial structure:

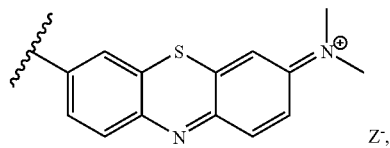

wherein Z is a counter ion, including chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Preferred anionic species of bisaminophenothiazine dyes salts include $Cl^-$, $Br^-$, $SCN^-$, $BF_4^-$, and $CH_3COO^-$. If the two aniline nitrogens of the bisaminophenothiazine dye are each disubstituted with methyl groups, then the dye is known as methylene blue (MB) with the chemical name 3,7-bis(dimethylamino)phenothiazine-5-ium chloride of the structure:

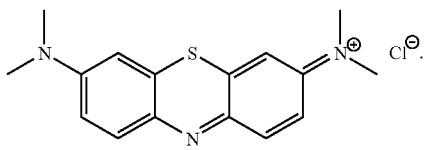

Other examples of bisaminophenothiazine dyes include 3,7-Bis(dimethylamino)-1,9-dimethylphenothiazin-5-ium chloride, N-[(3E)-7-amino-3H-phenothiazin-3-ylidene]methanaminium chloride, 7-(dimethylamino)-3H-phenothiazin-3-iminium chloride, N-(7-amino-3H-phenothiazin-3-ylidene)-N-methylmethanaminium chloride, and N-methyl-N-[7-(methylamino)-3H-phenothiazin-3-ylidene]methanaminium chloride. It is also intended that the term bisaminophenothiazine dye include the compound 1-[7-(1-piperazinyl)-3H-phenothiazin-3-ylidene]piperazin-1-ium bromide dihydrobromide.

The term "Alkyl", as used herein, means any straight chain or branched, non-cyclic saturated aliphatic hydrocarbon containing from 1 to 10 carbon atoms. Representative saturated straight chain alkyls include, but are not limited to, methyl, ethyl, n-propyl, n-butyl, n-pentyl, n-hexyl, n-septyl, n-octyl, n-nonyl, and the like; while saturated branched alkyls include, but are not limited to, isopropyl, sec-butyl, isobutyl, tert-butyl, isopentyl, and the like.

As related herein, "discoloration" means changing the natural color by making it duller or faded (e.g. dark blue to light blue or gray). It is not intended to be limited to entire removal of the color. The terms "immediately visually observing discoloration" mean that a person can view discoloration within a 10 second period.

As used herein, a "dye stable to a solution of hydrogen peroxide" means that the dye does not undergo discoloration when contacted with a 3% aqueous solution of hydrogen peroxide over a 1-hour period.

A "sample" of a solution means a segment or portion that is representative of a whole solution.

A solution "suspected" of containing hydroxyl radicals means any solution that might have hydroxyl radicals for any variety of reasons. It is intended to include solutions that have no hydroxyl radical presence or a low possibility or a high possibility of hydroxyl radical presence, and it is not intended to be limited to those solutions that have a high likelihood of having hydroxyl radicals.

Figure 7:
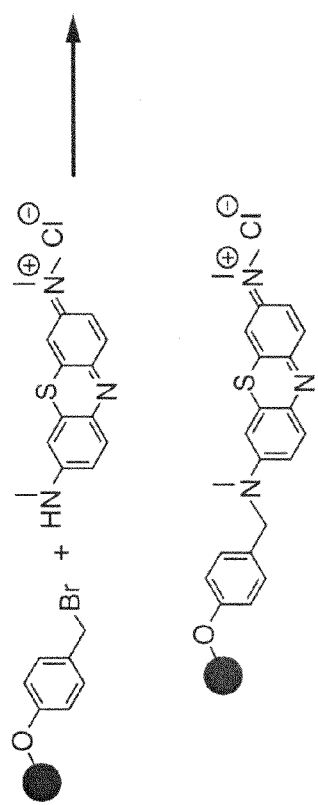
FIG. 7. Illustration of a method of immobilizing a dye to a polymer resin. One brominates Wang resin (polymer bound, 4-benzyloxybenzyl alcohol) in the presence of excess phosphorus tribromide. Reaction of the brominated resin with N-methyl-N-[7-(methylamino)-3H-phenothiazin-3-ylidene] methanaminium chloride provides the dye immobilized resin.

A "substrate" means the base layer of a structure. Substrates are preferably paper, alumina, glass or plastic (polymer). Substrates "containing a dye" or a dye "immobilized on a substrate" both mean that the substrate is in contact with the dye. For example, the substrate may be coated with the dye or the dye may be absorbed into the substrate or the dye may be covalently bound to the substrate. For example, a dye may be covalently bound to a polymer resin as depicted in FIG. 7.

A "quenching reagent of hydroxyl radicals" means any composition capable of preventing formation of or disintegration of the hydroxyl radical. It is not intended that the quenching reagent be limited by any particular mechanism of action. In preferred embodiments, hydroxyl radicals are formed by the reaction of hydrogen peroxide with iron $2^+$ cation, and the addition of the quenching reagent, e.g., sodium sulfite, may prevent the formation of hydroxyl radicals by disintegrating hydrogen peroxide and/or by disintegrating hydroxyl radicals and/or by reducing iron $3^+$ to iron $2^+$.

A "liquid transferring mechanism" means any of a variety of instruments that can transfer a sample of liquid solution from one location to another. It is not intended to be limited in the manner or mechanism in which the sample is obtained or transferred. For example a capillary tube, i.e. micropipette, obtains a sample of solution by exposing a cylinder to the surface of a solution causing surface tension and capillary action to cause the sample to rise inside the area of the tube. Once the sample is inside the cylinder, contacting the liquid sample with a solid typically discharges it. Other examples of liquid transferring mechanisms include eyedroppers and pipettes that typically operate by suctioning the sample from a solution. In another example, the liquid transferring mechanism maybe a wood, plastic, or metal stick that when placed in the appropriate liquid causes a sample to adhere to the surface which can then be wiped off at another location.

Remediation of Methylene Blue Waste

Methylene blue is used to stain garments. Thus, methods of decomposing waste solutions containing methylene blue are described. In particular, Dutta et al. Journal of Hazardous Materials B84: 57-71 (2001) involves remediation of methylene blue dye as a waste, and the reaction of the aqueous methylene blue dye with hydroxyl radicals. The reaction of the methylene blue with hydroxyl radicals occurs in an aqueous solution requiring an extended time, e.g., several hours, for substantial discoloration.

Titanium oxide based photocatalysts have been described to degrade methylene blue. Reviewed in, Rajeshwar et al., Pure Appl. Chem. 73(12):1849-1860 (2001). In Houas et al., Applied Catalysis B: Environmental 31: 145-157 (2001) titanium dioxide and ultraviolet light is used to degrade methylene blue in aqueous suspensions. In these references, the methylene blue is being remediated as a waste rather than being used for the detection of hydroxyl radicals. The reaction of the methylene blue occurs in the aqueous phase; however, in preferred embodiments of the invention, the methylene blue reaction occurs on a paper test strip pre-dried with a methylene blue dye.

Methylene Blue as an Indicator

In Ohko et al., J Biomed Mater Res (Appl Biomater) 56: 97-101 (2001) methylene blue dye coated on a $TiO_2$ surface is photocatalytically bleached indicating oxidative decomposition of the dye on the surface. It is believed that superoxide generated from oxygen gas is causing the decomposition of methylene blue. The titanium dioxide is coated on a silicone catheter and heat-treated at 110° C. for 15 minutes.

Read U.S. Pat. No. 6,790,411 (2004) discloses vaporous hydrogen peroxide indicator dyes that discolor in the presence of hydrogen peroxide. Read does not mention methylene blue. It is believed that methylene blue would not work as a dye in Read to detect hydrogen peroxide because methylene blue is not timely decomposed by the presence of hydrogen peroxide.

References disclose the use of methylene blue in oxygen or peroxide indicator systems because methylene blue may be reversibly reduced to a colorless intermediate in the presence of a reducing agent. Thus, systems have been created that use the appearance of blue color (methylene blue) as an indication of oxidative species correlating the depletion of a reductive environment.

For example, in Davies et al., U.S. Pat. No. 4,863,627 (1989) a contact lens cleaning composition contains hydrogen peroxide as a disinfecting agent, a delayed-release form of sodium thiosulfate for decomposing hydrogen peroxide over time, and methylene blue. In Davies, hydroxyl radicals are not decomposing methylene blue. The methylene blue is used to indicate that hydrogen peroxide has been entirely reduced by sodium thiosulfate. In Davies, the methylene blue changes from colored to colorless, but not because of the presence of hydroxyl radicals, instead because of the complete reduction of hydrogen peroxide by sodium thiosulfate. Contrarily, for embodiments of the current invention, methylene blue is used to correlate the existence of hydroxyl radicals by a blue (hydroxyl radical absent) to a clear (hydroxyl radical present) color. In another example, Sumitani et al., Analytical Sciences 20:1153-1157 (2004) discloses a composition containing methylene blue used to create an oxygen indicator. The reference describes a reversible oxidation/reduction process that occurs to methylene blue causing the paper strips containing the hybrid composition to turn blue in the presence of oxygen. In Sumitani, the methylene blue changes from colored to colorless, but not because of the presence of hydroxyl radicals, instead because of reductive species.

Droycon Bioconcepts Inc. market an aerobic degrading bacteria used to degrade organic pollutants such as hydrocarbons. The Bio-Remediation Bacteria (BRB) Tester BART System™ (BRB-BART) examines the loss of oxygen in the culturing sample as the bacteria become more active. When oxygen is depleted then the methylene blue based test indicator changes from a blue (oxygen/oxidative species present) color to a clear (oxygen/oxidative species absent) state. Contrarily, for embodiments of the current invention, methylene blue is used to correlate the existence of hydroxyl radicals by a blue (hydroxyl radical/oxidative species absent) color to a clear (hydroxyl radical/oxidative species present) state.

Methylene Blue Dye Test of Hydroxyl Radicals

An aqueous methylene blue dye test was tried first as a method of detecting hydroxyl radicals. However, it soon became apparent that an aqueous methylene blue dye test was not preferred because the color change of the methylene blue dye due to the presence of hydroxyl radicals occurred only after a lengthy period of time (~40 minutes). A methylene blue dye test strip was developed as an alternative to this aqueous method and provides a rapid (immediate) correlation of hydroxyl radical presence. In preferred embodiments of the invention, the methylene blue reaction occurs on a paper test strip with a pre-dried methylene blue dye.

In an aqueous phase reaction where molecules are allowed to collide in 3-dimensional space, the reaction is dependent on the concentration of the colliding species. It is preferred to use a dyed paper, since the methylene blue dye is soaked into and onto the paper fibers. Although it is not intended that the embodiment of the invention be limited by any particular mechanism, it is believed that the oxidation of methylene blue by the hydroxyl radicals is aided by the greater surface area available for the reaction and a higher concentration, resulting in a higher rate of reaction.

The more rapid detection of hydroxyl radicals by the methylene blue dye test strips was not predictable. The rapid detection of the presence of hydroxyl radicals during a Fenton's remediation process is advantageous, not only for a verification of the production of hydroxyl radicals during the remediation, but also for a determination of when quenching is complete.

In some embodiments, the invention relates to a method of detecting hydroxyl radicals using a paper test strip containing methylene blue dye. Methylene blue dye is decolorized when contacted with a solution containing hydroxyl radicals. Thus, the paper test trips become "bleached" (or at least partially bleached) when they come in contact with an aqueous solution of Fenton's reagent. These test strips are particularly useful during a remediation operation because the frequent "real time" monitoring of a remediation effort with these test strips containing methylene blue prevents the wasteful application of excess hydrogen peroxide (and hydrogen peroxide neutralizing agents such as sodium sulfite). The instant method is superior to previously described methods of detecting hydroxyl radicals because previously described methods indirectly indicate the presence of hydroxyl radicals by the formation of derivative compounds that are subsequently detected by more cumbersome non-visual means.

Existing methods use large sample volumes, while embodiments of the present invention use very small volumes (approximately 40 µL) of sample for the test strip method. The embodied methods also allow an investigator to determine when quenching of hydroxyl radicals is complete, i.e., the point where the concentration of hydroxyl radicals is substantially zero. Thus, a test strip method has a number of advantages including (a) the rapid nature of hydroxyl radical detection, (b) the small sample volume, (c) the lack of specialized equipment, (d) the lack of interaction with the reaction mixture, (e) the stability of the test strip when stored, and (f) the inexpensive nature of the method.

Other methods are distinct from embodiments of the current invention because they are focused on: (a) a different mechanism of decomposition of methylene blue based on the reaction of hydrogen peroxide, (b) decomposition of methylene blue as a waste product, and/or (c) detecting oxygen and hydrogen peroxide and not hydroxyl radicals.

Generation of hydroxyl radicals by an aqueous Fenton's reagent system was evaluated by a benzoic acid chemical probe method that detects hydroxyl radicals using thin layer chromatography and spectrophotometric wavelength scans. The presence of hydroxyl radicals was indirectly determined through the detection of hydroxylated benzoic acids. A Fenton's reagent reaction with ultra-pure (Milli-Q) water and a $Fe^{2+}$: $H_2O_2$ molar ratio of 1:20 generated hydroxyl radical containing samples. The presence and absence of hydroxyl radicals was determined prior to and following quenching of the Fenton's reaction mixture with 10% sodium sulfite, respectively. Bleaching of the methylene blue dye, due to the presence of hydroxyl radicals in a sample, was indicated by a discoloration from dark blue color to an almost white color, concentrated at the point of application, with a dark blue outline. A lack of bleaching indicates the absence of hydroxyl radicals in a sample and the completion of quenching. The results indicating the presence of hydroxyl radicals were verified in benzoic acid chemical probe experiments by the detection of hydroxylated benzoic acids on the developed thin layer chromatography plates, a violet solution color, and a peak absorbance at a wavelength close to 520 nm. These results suggest that the absence of hydroxyl radicals were likewise verified by an absence of these aforementioned observations.

In some embodiments the invention relates to a methylene blue dye test that qualitatively indicates the presence of hydroxyl radicals through an immediate, distinct bleaching of the methylene blue dye on a paper test strip after an aqueous Fenton's remediation sample containing hydroxyl radicals is applied to the test strip. This method provides a rapid qualitative indication of the presence of hydroxyl radicals with a simple procedure requiring inexpensive materials, and does not interfere with the reaction mixture by the addition of competitive probe chemicals. Methylene blue is a basic dye of the thiazine series used for dying and printing on cloth.

Although it is not intended that the invention be limited by any particular mechanism, it is believed that in the methylene blue dye test, the hydroxyl radical reacts with the methylene blue cation to produce a hydroxide ion and a methylene blue radical cation. Since the methylene blue cation is a dark blue in color and the methylene blue radical cation is colorless, application of a sample containing hydroxyl radicals to methylene blue dye will result in a change of color from dark blue to colorless. The reaction that causes the bleaching of the methylene blue dye is not dependent on $H_2O_2$. To standardize the methylene blue test, test strips were developed such that each has a consistent, uniform methylene blue dye section onto which samples could be applied and tested.

A Fenton system was used as a source of hydroxyl radicals to test the applicability of the methylene blue dye test toward the detection of hydroxyl radicals. In the Fenton's reagent process highly reactive hydroxyl radicals are produced by the oxidation of ferrous iron and the reduction of hydrogen peroxide. The classical procedure of the Fenton's reagent treatment consists of the addition of hydrogen peroxide in the presence of ferrous iron to a solution or suspension of compounds to be treated. The oxidation efficiency of the Fenton's type reaction depends of the $Fe^{2+}$:$H_2O_2$ ratio and the pH value. The optimal pH for the Fenton's reagent reaction efficiency is between pH 3 and 5. At more basic pH values, the iron is converted from a hydrated ferrous form to a colloidal ferric form, thereby causing a decrease in the effectiveness of the reaction. Fenton's reagent is an effective method of remediating contaminated soils and aqueous solutions through oxidation by hydroxyl radicals, which readily degrade a wide variety of organic pollutants. Rapid, inexpensive detection of the presence of hydroxyl radicals allows for immediate monitoring of the Fenton's remediation process and aids in optimizing the degradation efficiency. The ability of the methylene blue dye test to detect the presence/absence of hydroxyl radicals in a Fenton's reaction aqueous solution was verified by benzoic acid chemical probe hydroxyl radical detection methods using thin layer chromatography and spectrophotometric wavelength scans.

Fenton's Reaction in Ultra-Pure (Milli-Q) Water (No Benzoic Acid Addition)

The MB dye test was evaluated to determine the presence of hydroxyl radicals generated by the Fenton's reaction. As shown in FIG. 1, A, the MB dye test control strip (no sample added) was homogeneously dark blue in color. When the MB dye test was performed with ultra-pure (Milli-Q) water (FIG. 1, B), no bleaching or discoloration of the MB dye was observed. During the Fenton's reaction experiment prior to quenching, no significant change in solution pH (~pH 3.0) and temperature (23.0° C.) occurred during the 60-minute reaction period. In addition, this unquenched Fenton's reaction mixture remained clear and colorless in appearance. As shown in FIGS. 1, C and D, strips tested with unquenched Fenton's reaction mixture at 15 and 30 minutes, respectively, indicated the presence of hydroxyl radicals by an immediate bleaching of the MB dye.

The Fenton's reaction was quenched after 60 minutes. The pH of the reaction mixture increased from 3.121 to 7.716. The temperature was 22.5° C. The color of the reaction mixture changed from colorless to light orange, which can be attributed to the more basic pH of the reaction mixture during the quenching process, resulting in the conversion of iron from a hydrated ferrous form to a colloidal ferric form and the formation of ferric hydroxide ($Fe(OH)_3$). To verify, qualitatively, that quenching was complete, a MB dye test was performed. As shown in FIG. 1, E, a MB dye test of the Fenton's reaction mixture quenched with 30 drops (1.23 mL) of quenching agent produced very slight bleaching as indicated by light blue discoloration with no dark blue outline. As shown in FIG. 1, F, the addition of 5 more drops (0.21 mL) of 10% $Na_2SO_3$ to the reaction mixture resulted in a complete absence of bleaching, indicating that quenching was complete and no hydroxyl radicals remained.

Benzoic Acid in an Unquenched Fenton's Reaction Mixture

An experiment involving Fenton's reaction and the addition of Benzoic Acid (BA) was performed to verify the presence of hydroxyl radicals. Since BA is only slightly soluble in water at pH 3, the remaining BA was allowed to remain floating on the aqueous surface or suspended in solution. The addition of BA to the reaction mixture did not significantly alter the pH. Following initiation of the Fenton's reaction by addition of 3% $H_2O_2$, the reaction mixture appearance changed from colorless to a light pink color. No significant change in solution pH (~pH 3.0) and temperature (23.0° C.) occurred during the 120 minute reaction period.

The reaction mixture continued to darken in color to violet (at 30 minutes) and eventually dark violet (at 60 minutes), corresponding to the gradual dissolution of BA. Complete dissolution of BA occurred by 90 minutes through reaction with hydroxyl radicals to form more soluble hydroxylated benzoic acids (HBAs). One possible explanation for the change in reaction mixture color to dark violet is the hydroxylation of BA by hydroxyl radicals to form salicylic acid (2-hydroxybenzoic acid, 2-HBA), followed by the formation of a tetraaquosalicylatroiron (III) complex with $Fe^{3+}$. This violet complex is formed under an acidic pH and is characterized by peak absorption at a wavelength of 520 nm. The formation of other colored products resulting from the hydroxylation of BA should not be excluded.

Following the addition of 3% $H_2O_2$ to the reaction mixture, the reaction was monitored by performing TLC, as presented in FIG. 2. The first two TLC plates, FIGS. 2, A and B, were spotted with the standards 9 mM BA/MeOH and 9 mM 4-HBA/MeOH, respectively. From the results of these plates it was possible to distinguish the BA from the 4-HBA in the mixed standard. The remainder of the TLC plates (FIGS. 2, C-F) was spotted with the mixed standard. For the TLC plates in FIGS. 2, A to C, the Fenton's sample was obtained after 30 minutes of reaction, while for FIGS. 2, D, E, and F, the sampling times were 60, 90, and 120 minutes, respectively. The elution time for each TLC plate was approximately 10 minutes.

The BA consistently traveled a farther distance on the plate than the 4-HBA, which was darker in intensity than the BA. The products present in the reaction mixture changed as the reaction proceeded. The TLC plates at 30 minutes and 60 minutes, FIGS. 2, C and D, respectively, indicated one major product in a larger amount and numerous products present in smaller amounts (a series of smaller connected spots). However, at 90 minutes, FIG. 2, E, one major product in a larger amount, numerous products in smaller amounts, and two secondary products were observed. At 120 minutes, FIG. 2, F, two major products were observed with numerous products present in smaller amounts.

For all the Fenton's samples, none of the major spots correlated with either the BA or 4-HBA standards on the same plate, suggesting that the major spots are more likely HBA products other than 4-HBA. Retention factor ($R_f$) values were only calculated for major spots and are presented in Table 1 (Plates A-F). The spots were numbered with the spot of farthest migration labeled as 1 and the remaining spots numbered consecutively. For all the Fenton's samples, the $R_f$ values of the major spots were significantly different (>0.05) from the $R_f$ values calculated for BA and 4-HBA standards on the same plate. However, the visual correspondence between the numerous products present in smaller amounts and the 4-HBA standard spot suggests that 4-HBA was produced in a small quantity. The presence of HBAs on the developed TLC plate for the Fenton's reaction mixture sample verified that hydroxyl radicals were present in the reaction solution to react with the added BA. Comparing TLC plates, based on the absolute difference in the $R_f$ values, spot 1 of the Fenton's samples from 30 minutes, 60 minutes, 90 minutes, and 120 minutes of reaction time are most likely the same compound. Furthermore, spot 2 of the Fenton's sample from 120 minutes is most likely the same compound as spot 3 of the Fenton's sample from 90 minutes.

of unquenched Fenton's reaction mixture containing BA at 0 minutes to 120 minutes of elapsed reaction time. As the reaction time increased, there was an increase in the absorbance value for each wavelength correlating with the increase in the intensity of the violet color of the reaction mixture. The maximum absorbance value (peak absorbance) occurred at a wavelength of 517 nm as the tetraaquosalicylatroiron (III) complex was generated. The violet color of the reaction mixture and the peak absorbance at a wavelength close to 520 nm are indications of the formation of HBA products and verify the presence of hydroxyl radicals. The FIG. 3 inset illustrates the increase in absorbance at 517 nm with an increase in the reaction time.

Figure 4:
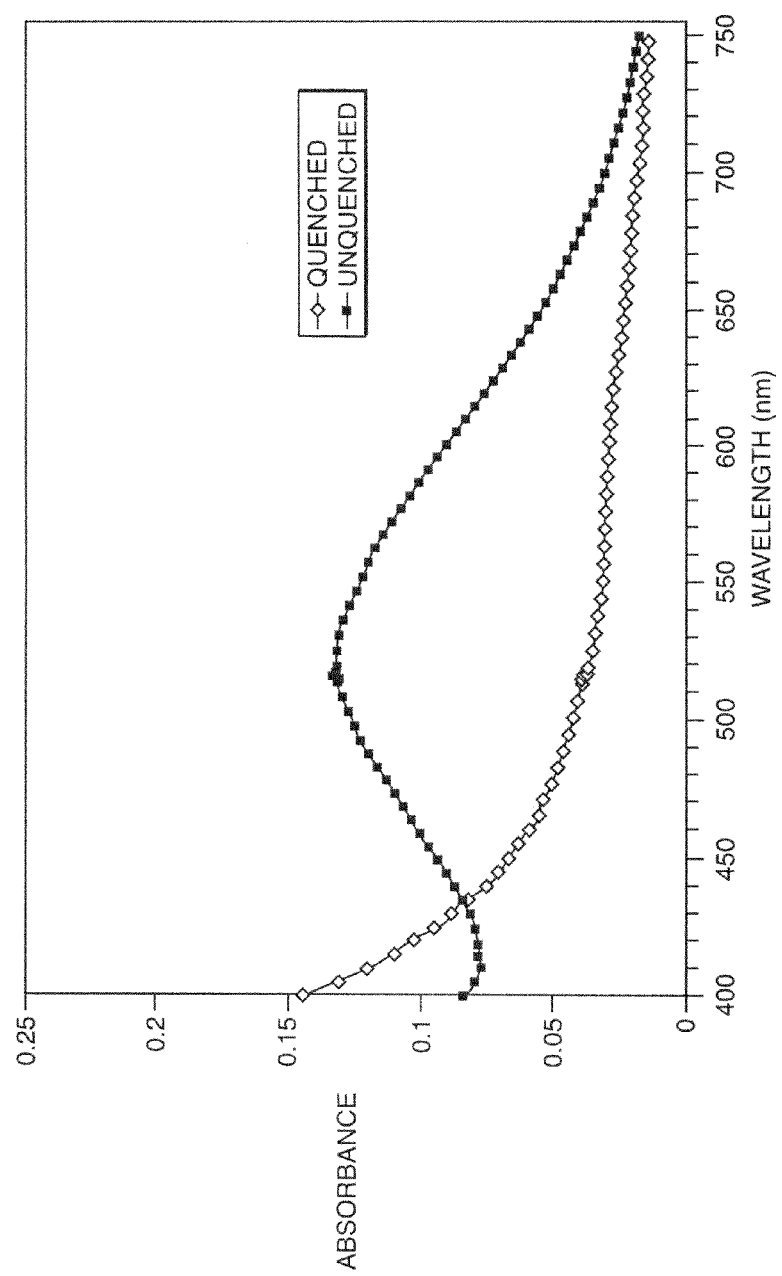
FIG. 4. Wavelength scans of the effect of quenching an unquenched Fenton's reaction mixture containing a benzoic acid chemical probe at 45 minutes of reaction time. Wavelength scans were performed over a wavelength range of 400 nm to 750 nm. After performing a wavelength scan on a 1000 µL sample of Fenton's reaction mixture from 45 minutes of reaction time, 25 µL of 10% sodium sulfite quencher was added to the sample. Following mixing, a wavelength scan was performed on the quenched sample.

After performing a wavelength scan on a 1000 μL sample of the unquenched Fenton's reaction mixture containing BA at 45 minutes of reaction time, 25 μL of 10% $Na_2SO_3$ was mixed into the sample in the cuvette. The violet color of the solution was immediately replaced by a light yellow color. A wavelength scan was then repeated over a wavelength range of 400 nm to 750 nm. FIG. 4 presents the wavelength scan of the unquenched Fenton's reaction mixture containing BA after 45 minutes of reaction time alongside the wavelength scan of the same sample following quenching. Unlike the unquenched wavelength scan in which a peak absorbance occurred at 517 nm, for the quenched wavelength scan there was a loss of this peak absorbance corresponding with the disappearance of the violet color of the Fenton's reaction mixture. The disappearance of the violet color can be explained as the reduction of $Fe^{3+}$ to $Fe^{2+}$ by $Na_2SO_3$ (reducing agent) resulting in loss of the tetraaquosalicylatroiron (III) complex. In addition, the $Na_2SO_3$ quenched the hydroxyl radicals in the reaction mixture, thereby preventing further formation of salicylic acid by the hydroxylation of BA. The light yellow color can be attributed to the more basic pH of the reaction mixture during the quenching process as previously described. Since the formation of the tetraaquosalicylatroiron (III) complex is preferred in acidic conditions, the presence of $Fe^{3+}$ in the quenched reaction mixture does not result in the reforming of the complex.

TLC of an Unquenched Fenton's Reaction Mixture in the Absence of Benzoic Acid (BA) Addition To verify that the unquenched TLC results of the preceding section were due to the reaction of BA with hydroxyl radicals, the same experiment was repeated without the addition of

TABLE 1

Retention Factor ($R_f$) Results for Benzoic Acid Chemical Probe in an Unquenched (Plates A-F) and Quenched (Plates G-J) Fenton's Reaction Mixture

| Plate # | Standard Type | | Standard $R_f$ | | ReactionTime | Fenton Sample $R_f$ | | |
|---|---|---|---|---|---|---|---|---|
| | Single | Mixed | BA | HBA | (minutes) | Spot 1 | Spot 2 | Spot 3 |
| A | • | | 0.54 | | 30 | 0.46 | | |
| B | • | | | 0.35 | 30 | 0.48 | | |
| C | | • | 0.54 | 0.33 | 30 | 0.48 | | |
| D | | • | 0.53 | 0.35 | 60 | 0.47 | | |
| E | | • | 0.52 | 0.36 | 90 | 0.46 | 0.22 | 0.10 |
| F | | • | 0.52 | 0.35 | 120 | 0.44 | 0.13 | |
| G | • | | 0.51 | | 30 | 0.49 | | |
| H | • | | | 0.32 | 30 | 0.51 | | |
| I | | • | 0.50 | 0.34 | 30 | 0.52 | | |
| J | | • | 0.47 | 0.33 | 90 | 0.51 | | |

Figure 3A:
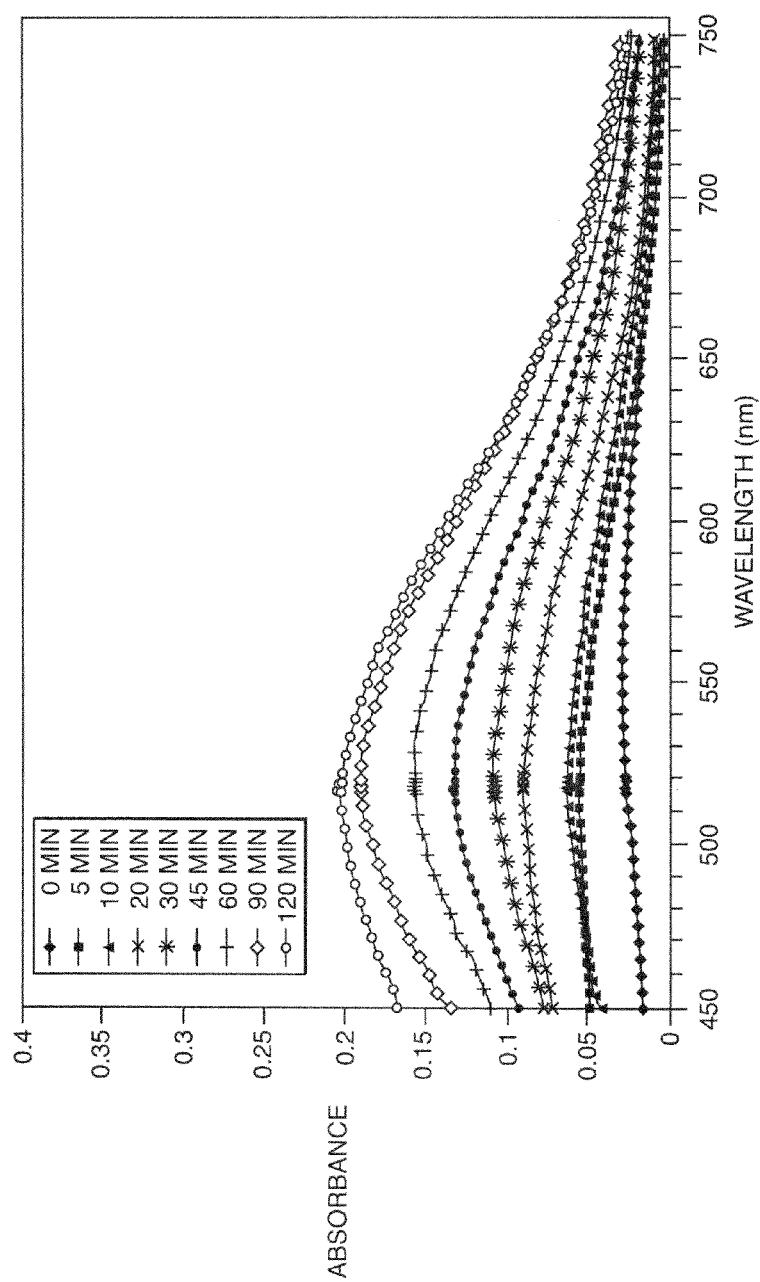
FIG. 3. Wavelength scans (absorption spectra) of unquenched Fenton's reaction mixture with a benzoic acid chemical probe. Wavelength scans were performed over a wavelength range of 450 nm to 750 nm. Each wavelength scan represents a Fenton's reaction mixture sample at a different reaction time ranging from 0 minutes to 120 minutes after initiation of the Fenton's reaction. Absorbance vs. reaction time of unquenched Fenton's reaction mixture with a benzoic acid chemical probe at the wavelength of 517 nm is shown in the inset. Each data point is representative of the absorbance at 517 nm obtained from the wavelength scan of the Fenton's reaction mixture at a particular reaction time.
Figure 3B:
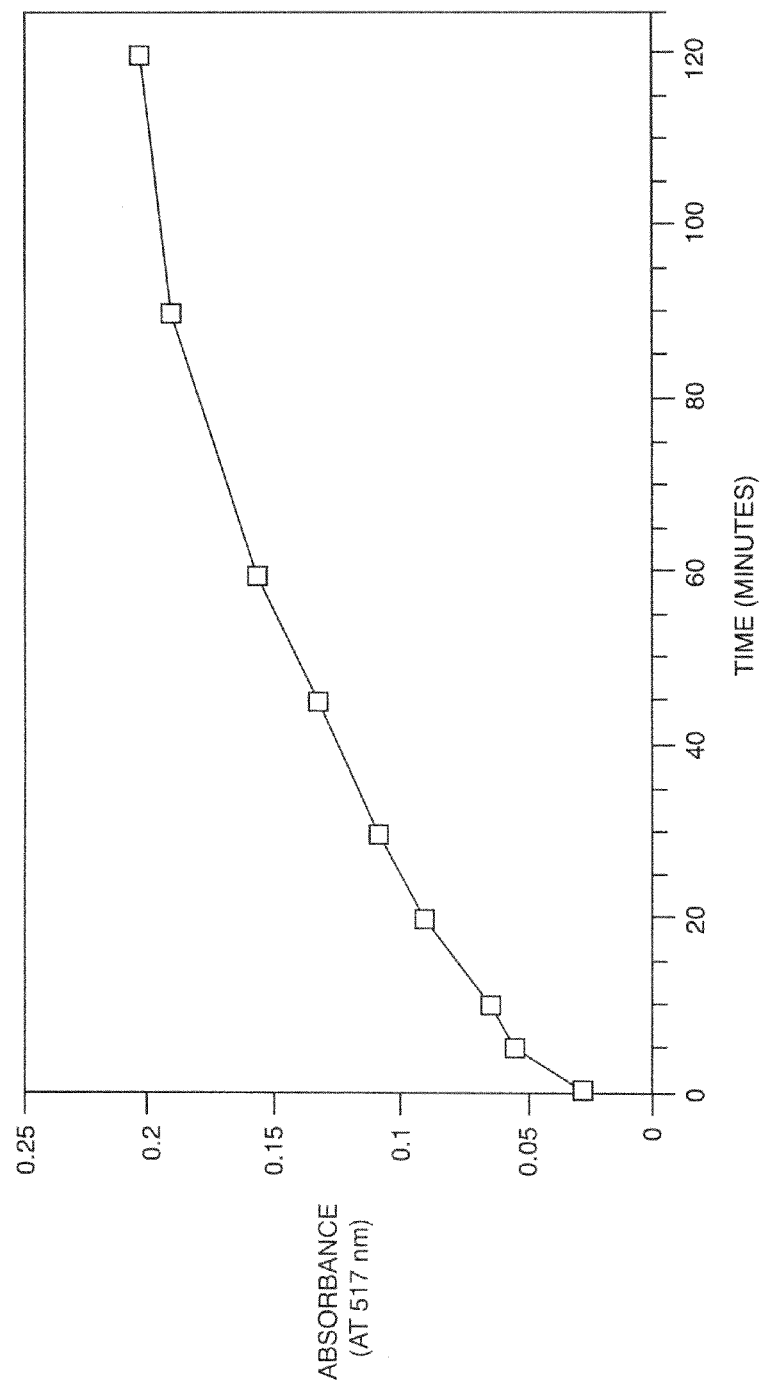

The change in color of the Fenton's reaction mixture to dark violet was monitored by spectrophotometric wavelength scans. FIG. 3 presents the wavelength scans over a visible wavelength range of 450 nm to 750 nm on 1000 μL samples BA. No significant change in solution pH (~pH 3.0) and temperature (22.5° C.) occurred throughout the 60 minute reaction period. The reaction mixture remained clear and colorless following initiation of the Fenton's reaction by addition of 3% $H_2O_2$, indicating that change in coloration to violet depends on the presence of both BA and hydroxyl radicals. This observation was further supported by using benzoic acid in an unquenched Fenton's reaction mixture experiment, in which no color change to pink occurred in the reaction solution with the presence of BA until after the addition of 3% $H_2O_2$, resulting in the presence of hydroxyl radicals. No spots appeared on the TLC plate for the Fenton's reaction mixture sample at 30 minutes and 60 minutes of reaction time, indicating that the spots observed above the origin on the developed TLC plates for the benzoic acid in an unquenched Fenton's reaction mixture experiment were a result of the reaction of BA with hydroxyl radicals.

Benzoic Acid in a Quenched Fenton's Reaction Mixture.

An experiment, involving Fenton's reaction and the addition of BA following the completion of quenching, was performed to verify the absence of hydroxyl radicals in the reaction mixture. In the reaction prior to quenching, the pH (~pH 3.0) and temperature (22.0° C.) remained constant and the reaction mixture remained clear and colorless. After 60 minutes of reaction time, the Fenton's reaction was quenched, and the reaction mixture changed to light orange, attributable to the more basic pH of the reaction mixture during the quenching process. The pH ranged from 7.5 to 7.6 and the temperature remained at 21.0° C. MB dye tests were performed to determine the completion of quenching, which occurred after the addition of 40 drops (1.76 mL) of 10% $Na_2SO_3$.

Following the addition of BA to the reaction mixture, the pH slowly decreased from 7.6 to 4.6 after 90 minutes, and the temperature remained constant at 21.0° C. The BA dissolved in the reaction mixture slightly faster than what was observed in using benzoic acid in an unquenched Fenton's reaction mixture experiment, achieving complete dissolution in 60 minutes. The more rapid dissolution of BA can be explained by the higher solubility of BA at a pH of 7.6 versus that at a pH of 3. The reaction solution remained light orange following the addition of BA after quenching, further supporting that the pink to violet color change is dependent on the presence of both BA and hydroxyl radicals. In the absence of hydroxyl radicals and at a basic pH, the salicylic acid and ultimately the tetraaquosalicylatroiron (III) complex cannot form.

Following the addition of BA, the reaction was monitored by performing TLC. For all the Fenton's reaction mixture samples, only one spot appeared on the TLC plate above the origin and correlated with the BA standard, as supported by the $R_f$ calculations presented in Table I (Plates G-J). The Fenton's reaction mixture spot had an $R_f$ range of 0.49 to 0.52. Since the maximum absolute $R_f$ difference between the Fenton's reaction mixture spot and the BA standard spot on the same plate was 0.04, these spots are assumed to be the same compound. The absence of HBAs on the TLC plate results for the Fenton's reaction mixture sample verified that quenching was complete, and no hydroxyl radicals were present in the solution when BA was added.

Figure 5:
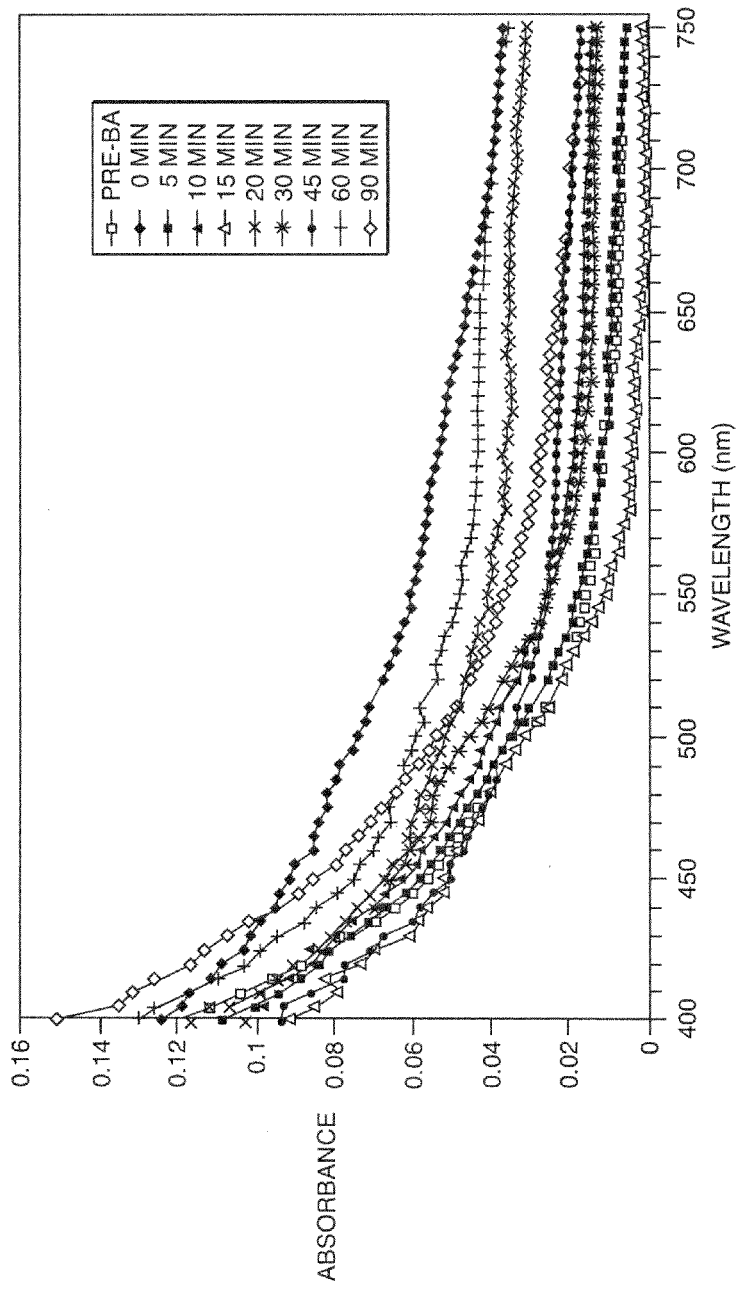
FIG. 5. Wavelength scans (absorption spectra) of quenched Fenton's reaction mixture. Wavelength scans were performed over a wavelength range of 400 nm to 750 nm. The "Pre-BA" wavelength scan represents a sample of the Fenton's reaction mixture prior to the benzoic acid chemical probe addition, but after completion of quenching. The remainder of the wavelength scans represents Fenton's reaction mixture samples at 0 to 90 minutes following the addition of benzoic acid after the completion of quenching.
Figure 6:
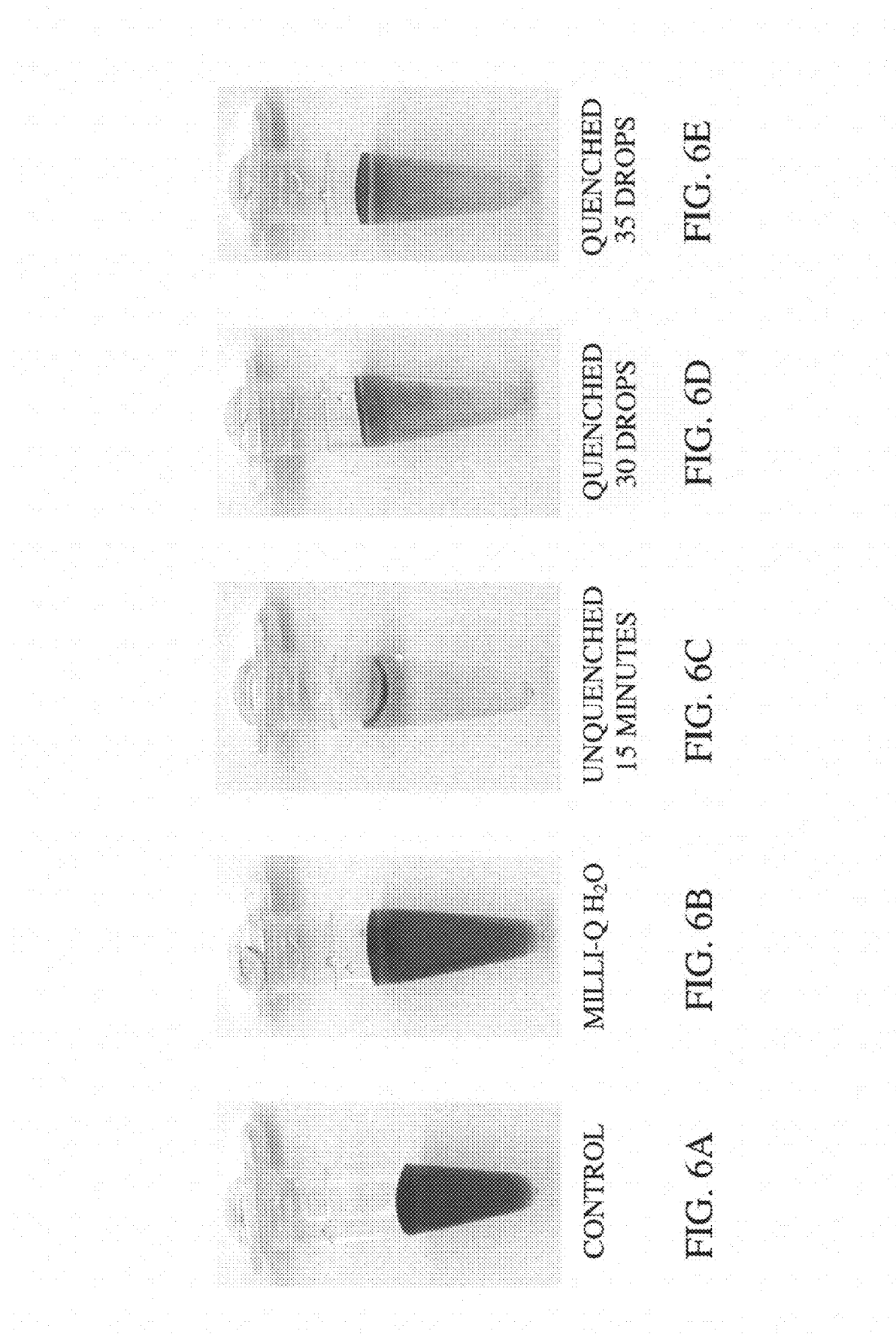
FIG. 6. Aqueous methylene blue dye test results as they appeared 40 minutes after the addition of the test sample. In vial A no sample was added to the methylene blue dye in the control vial. The dye was a dark blue. In vial B, 60 µL of Milli-Q $H_2O$ was added to the methylene blue dye. The dye became very slightly lighter blue in color, which can be attributed to dilution. In vial C, 15 minutes after the initiation of the Fenton's reaction, a 60 µL sample of the unquenched Fenton's reaction mixture was added to the methylene blue dye. Immediately following the addition of the sample, the dye color was indistinguishable from that observed in the Milli-Q $H_2O$ test (Vial B). However, after 40 minutes, the dye appeared to have bleached and became a very light gray color. In vial D an aqueous methylene blue dye test of the Fenton's reaction mixture is quenched with 30 drops of 10% $Na_2SO_3$ solution. Immediately following the addition of the sample, the dye color was indistinguishable from that observed in the Milli-Q $H_2O$ test (Vial B). After 40 minutes, the dye appeared only slightly lighter in color than that observed in the Milli-Q $H_2O$ test (Vial B). In vial E an aqueous methylene blue dye test of the Fenton's reaction mixture is quenched with 35 drops of 10% $Na_2SO_3$ solution. Immediately following the addition of the sample, the dye color was indistinguishable from that observed in the Milli-Q $H_2O$ test (Vial B). After 40 minutes, the dye appeared only slightly lighter in color than that observed in the Milli-Q $H_2O$ test (Vial B) and was indistinguishable from the Vial D (quenched 30 drops) results. Since no bleaching was distinctly observed, it was assumed that quenching was complete.

The absence of hydroxyl radicals following quenching was also assessed by spectrophotometric wavelength scans over a wavelength range from 400 nm to 750 nm. Prior to the BA addition but after completion of quenching, a wavelength scan was performed on the reaction mixture to compare to the effect of BA. The results of this wavelength scan, identified as "Pre-BA," as well as wavelength scans performed on 1000 μL samples of quenched Fenton's reaction mixture from 0 to 90 minutes after the addition of BA, are presented in FIG. 5. The wavelength scan results, following the addition of BA, did not vary significantly from that observed for "Pre-BA." The absence of peak absorbance at close to 520 nm was an indication of the lack of HBA products in the reaction mixture and suggests the absence of hydroxyl radicals. Since no hydroxyl radicals were present in the quenched reaction mixture to react with the added BA, the tetraaquosalicylatroiron (III) complex did not form.

Experimental

EXAMPLE 1

Fenton's Reagent Reaction with Milli-Q Water

A Fenton's reagent reaction with ultrapure water (Milli-Q) was performed to generate hydroxyl radicals containing samples for the methylene blue dye test, thin layer chromatography, and spectrophotometric wavelength scan experiments. For the Fenton's reaction, an $Fe^{2+}:H_2O_2$ molar ratio of 1:20 was selected for study. The initial concentration of $H_2O_2$ in the reaction mixture was 3 mM. The initial $Fe^{2+}$ concentration preferred for the $Fe^{2+}:H_2O_2$ ratio was 0.15 mM. Since it was difficult to accurately measure the exact amount of ferrous sulfate heptahydrate ($FeSO_4.7H_2O$) to prepare a 0.15 mM solution, a 5.0 mM $FeSO_4$ stock solution was first prepared from $FeSO_4.7H_2O$ and water, and appropriately diluted. The pH of the $FeSO_4$ was adjusted to 3 by drop-wise addition of appropriate amounts 0.5 M $H_2SO_4$ and 1 M NaOH.

The Fenton's reaction was initiated by the addition of 3% hydrogen peroxide to the reaction solution providing an initial concentration of 3 mM of hydrogen peroxide. The 3% hydrogen peroxide solution was prepared from 30% unstablized hydrogen peroxide. Since stabilizing agents such as hydroxyl radical scavengers in commercial hydrogen peroxide might affect the experiments, only hydrogen peroxide devoid of stabilizing agents was used. In order to prevent localized reactions that might occur when a small volume of very concentrated solution is added to a reaction mixture and for ease of measurement, 3% rather than 30% solutions of hydrogen peroxide were used in the reaction initiation. The Fenton's reagent reaction was then allowed to occur for 60 minutes. To test, qualitatively, the production of hydroxyl radicals during the reaction, methylene blue dye tests were performed on the unquenched reaction mixture at 15, 30, and 60 minutes. The methylene blue dye test indicates the presence of hydroxyl radicals through an immediate, distinct, concentrated bleaching of the methylene blue dye from dark blue to almost white with a dark blue outline.

After 60 minutes, the Fenton's reaction was quenched by the drop-wise addition of a 10% aqueous solution of $Na_2SO_3$. To verify, qualitatively, that quenching was complete, 5 minutes after addition of the 10% aqueous $Na_2SO_3$ solution, a methylene blue dye test was performed on the quenched reaction mixture. The methylene blue dye test indicated that quenching was complete, i.e. no hydroxyl radicals were detected, by the absence of bleaching of the methylene blue dye. Additional 10% $Na_2SO_3$ solution was added to the reaction mixture and the methylene blue dye test was repeated until no discoloration of the methylene blue dye was observed, i.e. quenching was complete. Usually, quenching was complete after the addition of 30 to 35 drops or 1.0 to 1.5 mL of the 10% $Na_2SO_3$ solution per 100 mL of reaction mixture. If excess 10% $Na_2SO_3$ solution was added, a slight white residue was visible on the surface of the test strip.

EXAMPLE 2

Methylene Blue Dye Test

To standardize the methylene blue dye test, test strips were developed such that each has a consistent, uniform methylene blue dye section on which samples could be applied and tested. A 10 mM stock solution of methylene blue dye was prepared with methanol and stored in a 125 mL glass bottle in the dark. For test strip preparation, a 1.0 mM methylene blue dye solution was then prepared with ultra-pure water from the 10 mM methylene blue dye stock solution. Qualitative filter paper (Grade 1, 70 mm diameter circles, medium porosity) (Fisher Scientific, Hanover Park, Ill.) was cut into two rectangular test strips approximately 2 cm by 6 cm in size. Using a black, fine point, permanent marker, a horizontal line was made on both sides of the test strip about 1.5 cm from the bottom and allowed to dry. Permanent marker ink generally contains a dye, one or more alkylalcohols, e.g., n-propanol, n-butanol, and a ketone, e.g., diacetone alcohol. This marker line serves as a hydrophobic barrier that prevents the MB dye from spreading above this line during the dipping process. The bottom of the test strip was then dipped 10 times into 1.0 mM MB dye solution to the level of the marker line. The dipped test strip was then placed onto a paper towel-lined tray and allowed to completely dry in the dark. Dried strips stored for 24 hours were used in this study, however strips can be stored in a sealed, dark plastic bag for up to 33 days without adversely affecting test results.

The MB dye test was performed during the Fenton's reaction to verify the formation of hydroxyl radicals and during the quenching process to verify completion of quenching. The MB dye test was performed by placing 40 µL of an aqueous sample dropwise onto the center of the MB dyed section of a test strip, with the sample absorbing into the test strip between drops. All MB dye tests were compared against a test strip tested with ultra pure water. The absence of bleaching of the MB dye indicated that no hydroxyl radicals were present to the extent detectable by this qualitative test. In the quenching process of the Fenton's reaction, the absence of bleaching signified that quenching was complete. Bleaching of the MB dye, due to the presence of hydroxyl radicals in a sample, was indicated by an immediate discoloration of the MB dye from a dark blue color to an almost white color, concentrated at the point of application, with a dark blue outline.

EXAMPLE 3

Fenton's Reaction in Ultra Pure Water

A Fenton's reaction was performed to generate hydroxyl radicals in aqueous samples for the MB dye test, thin layer chromatography (TLC), and spectrophotometric wavelength scan experiments. All experiments were performed in ultra-pure water. For the Fenton's reaction, an $Fe^{2+}:H_2O_2$ molar ratio of 1:20 was used. The initial concentrations of $Fe^{2+}$ and $H_2O_2$ in the reaction mixture were 0.15 mM and 3 mM, respectively. For optimal Fenton's reaction efficiency, the $FeSO_4$ solution was adjusted to pH 3 with 0.5 M $H_2SO_4$ and/or 1 M NaOH. The pH was adjusted/monitored using a 720 A plus pH/ISE meter with an 8102 BNU Ross Ultra Combination pH electrode (ThermoOrion, Beverly, Mass.).

The Fenton's reaction was initiated by the addition of 3% $H_2O_2$ to the reaction mixture to obtain an initial concentration of 3 mM $H_2O_2$. The 3% $H_2O_2$ solution was prepared from 30% unstabilized $H_2O_2$ and ultra-pure water. Since stabilizing agents (hydroxyl radical scavengers) in commercial $H_2O_2$ might affect the results, $H_2O_2$ devoid of stabilizing agents was used. In order to prevent localized reactions (that might occur when a small volume of very concentrated solution is added to a reaction mixture), 3% $H_2O_2$ rather than 30% $H_2O_2$ was used to initiate the reaction. To test, qualitatively, the production of hydroxyl radicals during the reaction, MB dye tests were performed on the unquenched reaction mixture at 15, 30, and/or 60 minutes of reaction.

After 60 minutes, the Fenton's reaction was quenched with a 10% aqueous solution of $Na_2SO_3$ (quenching by the periodic addition of 2 to 3 drops of 10% $Na_2SO_3$ solution for every 10 mL of reaction mixture). To verify, qualitatively, that quenching was complete, 5 minutes after the addition of the 10% $Na_2SO_3$ solution, a MB dye test was performed. Additional 10% $Na_2SO_3$ solution was added to the reaction mixture and the MB dye test was repeated until no discoloration of the MB dye was observed (quenching was complete).

EXAMPLE 4

Hydroxyl Radical Detection by Benzoic Acid

To verify the ability of the MB dye test to detect the presence of hydroxyl radicals in a Fenton's reaction, experiments were performed using benzoic acid (BA) as a chemical probe. BA reacts with hydroxyl radicals to form o-, m-, and p-hydroxybenzoic acids as well as other products. The presence of hydroxyl radicals can be indirectly determined through the detection of these hydroxylated benzoic acids (HBAs) by performing TLC and spectrophotometric wavelength scans.

Two Fenton's reaction experiments were performed with the addition of BA. Finely ground BA was added to the Fenton's reaction solution to obtain a final concentration of 9 mM BA. The experiment of using benzoic acid in an unquenched Fenton's reaction mixture is similar to the procedure of the Fenton's reaction in ultra-pure water prior to quenching, except that BA was added immediately preceding the initiation of the Fenton's reaction by the addition of 3% $H_2O_2$. Following initiation, the reaction was monitored by performing TLC and spectrophotometric wavelength scans at various times throughout the reaction period (120 minutes). The objective was to verify the presence of hydroxyl radicals in the Fenton's reaction mixture, as was previously detected by the MB dye test. The second experiment, of using benzoic acid in a quenched Fenton's reaction mixture is similar to the procedure of the Fenton's reaction in ultra-pure water except that BA was added following the completion of quenching. TLC and spectrophotometric wavelength scans were performed at various times until 90 minutes had elapsed. A wavelength scan of the reaction mixture was also performed immediately preceding the addition of BA. The objective was to verify the absence of hydroxyl radicals in the Fenton's reaction mixture following the completion of quenching, as was previously detected by the MB dye test.

EXAMPLE 5

Thin Layer Chromatography (TLC) and Spectrophotometric Wavelength Scans

TLC was performed on the Fenton's reaction mixture during the BA experiments to detect hydroxylated benzoic acids (HBAs) as an indirect indication of the presence of hydroxyl radicals. An additional experiment, using the TLC of an unquenched Fenton's reaction mixture in the absence of benzoic acid addition was similar to the procedure of Fenton's reaction in ultra-pure water prior to quenching. Following initiation, the reaction was monitored by performing TLC at various times. The objective was to verify that the TLC results of using benzoic acid in an unquenched Fenton's reaction mixture were due to the reaction of BA with hydroxyl radicals.

TLC plates were spotted using Drummond 1 μL "Microcap" micropipettes (Fisher Scientific, Hanover Park, Ill.) onto 2.5×7.5 cm silica gel 60 $F_{254}$ precoated TLC plates with acid-stable fluorescent indicator (Fisher Scientific, Hanover Park, Ill.). The left side of the TLC plate was spotted with one of three selected standard solutions: 2 μL of 9 mM BA in methanol (MeOH), 1 μL of 9 mM 4-hydroxybenzoic acid (4-HBA) in methanol, or 2 μL of a mixed standard consisting of 50 μL 9 mM BA/MeOH and 25 μL 9 mM 4-HBA/MeOH. A volume of 3 μL of Fenton's reaction sample was spotted on the right side of the TLC plates. The origin, where the standard and sample were spotted, was marked near the bottom of the plate by two horizontal lines on either side of the plate. A solution of methanol:chloroform at a ratio of 1:5 was selected as the eluting solvent for developing the TLC plates. TLC plates were examined under short wave ultraviolet light and the resulting "spots" were carefully traced with a pencil with a dot marked in the center of maximum intensity. Retention factors ($R_f$) for each separated compound were calculated as the distance traveled by the compound measured to the point of maximum intensity divided by the distance traveled by the solvent front. The $R_f$ value of each compound separated from the Fenton's reaction sample was compared with the $R_f$ value of the standard on the same plate. An absolute $R_f$ difference of greater than 0.05 was considered to be a significant difference indicating that the compound was different from the standard. Fenton's reaction samples were scanned spectrophotometrically on a Beckman DU7400 spectrophotometer (Beckman Instruments, Fullerton, Calif.). Ultra-pure water was used as a blank.

The invention claimed is:

1. A method of determining the presence of hydroxyl radicals in a sample comprising:
   i) providing:
      a) a liquid sample and
      b) a substrate comprising a test area comprising 3,7-bis(dimethylamino)phenothiazine-5-ium chloride enclosed by a hydrophobic barrier, said 3,7-bis (dimethylamino)phenothiazine-5-ium chloride having a color that is stable to a solution of hydrogen peroxide; and
   ii) contacting said 3,7-bis(dimethylamino)phenothiazine-5-ium chloride with said sample under conditions such that immediate discoloration of said color of said substrate is observed in the presence of hydroxyl radicals, thereby determining the presence of hydroxyl radicals in said sample.

2. The method of claim 1, wherein said substrate is paper and said 3,7-bis(dimethylamino)phenothiazine-5-ium chloride, prior to step (ii), is dried on said paper.

3. The method of claim 1, wherein said hydrophobic barriers comprises an alkylalcohol and a ketone.

4. The method claim 1, wherein said sample contains hydrogen peroxide.

5. A method of determining the presence of hydroxyl radicals in a sample comprising:
   i) providing:
      a) a liquid sample and
      b) a dye stable to a solution of hydrogen peroxide, wherein said dye is a bisaminophenothiazine dye, immobilized on a paper substrate, said paper substrate having a color; and
   ii) contacting said bisaminophenothiazine dye with said sample under conditions such that immediate discoloration of said color of said substrate is observed in the presence of hydroxyl radicals, thereby determining the presence of hydroxyl radicals in said sample.

6. The method of claim 5, wherein said bisaminophenothiazine dye, prior to step (ii), is dried on said paper substrate.

7. The method of claim 5, wherein said paper is filter paper

8. The method of claim 5, wherein said substrate comprises one or more hydrophobic barriers enclosing said dye 9. The method of claim 5, wherein said sample contains hydrogen peroxide.

* * * * *

UNITED STATES PATENT AND TRADEMARK OFFICE
CERTIFICATE OF CORRECTION

| | |
|---|---|
| PATENT NO. | : 7,939,340 B2 |
| APPLICATION NO. | : 11/478959 |
| DATED | : May 10, 2011 |
| INVENTOR(S) | : Andrea Yuki Satoh et al. |

Page 1 of 1

It is certified that error appears in the above-identified patent and that said Letters Patent is hereby corrected as shown below:

In the Specification:

In column 1, line 3, please insert:

-- STATEMENT REGARDING FEDERALLY SPONSORED RESEARCH OR DEVELOPMENT

This invention was made with government support under ES049110 awarded by the National Institutes of Health. The government has certain rights in the invention. --

Signed and Sealed this
Twelfth Day of January, 2016

Michelle K. Lee
*Director of the United States Patent and Trademark Office*